United States Patent
Chowienczyk et al.

(10) Patent No.: US 10,213,116 B2
(45) Date of Patent: *Feb. 26, 2019

(54) METHODS FOR MEASURING BLOOD PRESSURE

(71) Applicant: SunTech Medical, Inc., Morrisville, NC (US)

(72) Inventors: Philip Jan Chowienczyk, London (GB); Sally Emma Brett, London (GB); Antoine Yves Marie Guilcher, London (GB)

(73) Assignee: SunTech Medical, Inc., Morrisville, NC (US)

(*) Notice: Subject to any disclaimer, the term of this patent is extended or adjusted under 35 U.S.C. 154(b) by 375 days.

This patent is subject to a terminal disclaimer.

(21) Appl. No.: 15/019,541

(22) Filed: Feb. 9, 2016

(65) Prior Publication Data

US 2016/0150983 A1     Jun. 2, 2016

Related U.S. Application Data

(63) Continuation of application No. 13/129,017, filed as application No. PCT/GB2009/002703 on Nov. 18, 2009, now Pat. No. 9,289,138.

(30) Foreign Application Priority Data

Nov. 18, 2008   (GB) .................................. 0821084.1

(51) Int. Cl.
   *A61B 5/022*     (2006.01)
   *A61B 5/00*     (2006.01)
   *A61B 5/021*     (2006.01)
   *A61B 5/02*     (2006.01)

(52) U.S. Cl.
    CPC .......... *A61B 5/02108* (2013.01); *A61B 5/022* (2013.01); *A61B 5/02116* (2013.01); *A61B 5/02225* (2013.01); *A61B 5/7271* (2013.01)

(58) Field of Classification Search
CPC combination set(s) only.
See application file for complete search history.

(56) References Cited

U.S. PATENT DOCUMENTS 5,265,011 A * 11/1993 O'Rourke .............. A61B 5/021
                                                    128/920
5,560,366 A     10/1996   Harada et al.
(Continued)

FOREIGN PATENT DOCUMENTS

EP         1179318       2/2002
JP       H03231631      10/1991
(Continued)

OTHER PUBLICATIONS

Gallagher, David, Audrey Adji, and Michael F. O'Rourke. "Validation of the transfer function technique for generating central from peripheral upper limb pressure waveform." (2004): 1059-1067 (Gallagher).*
(Continued)

*Primary Examiner* — Christian Jang
*Assistant Examiner* — Mitchell E Alter
(74) *Attorney, Agent, or Firm* — Myers Bigel, P.A.

(57) ABSTRACT

The application relates to an apparatus and a method for estimating a central systolic blood pressure (cSBP) of a subject, in which a peripheral blood pressure waveform of the subject's pulse and at least two peripheral blood pressure measurements within the cardiac cycle of the subject are determined and the peripheral blood pressure waveform is manipulated with a transfer function to provide an estimate of the central blood pressure waveform of the subject's pulse. The at least two peripheral blood pressure measurements within the cardiac cycle of the subject and the peripheral blood pressure waveform of the subject's pulse are determined at substantially the same point on a peripheral artery of the subject. The estimate of the central blood (Continued)

Figure 1:
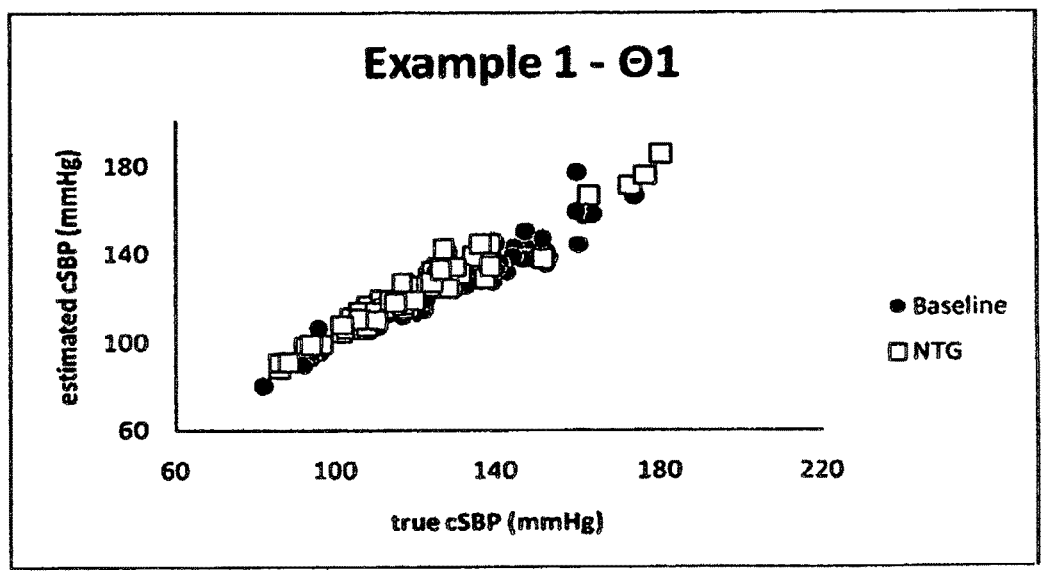
Figure 1:
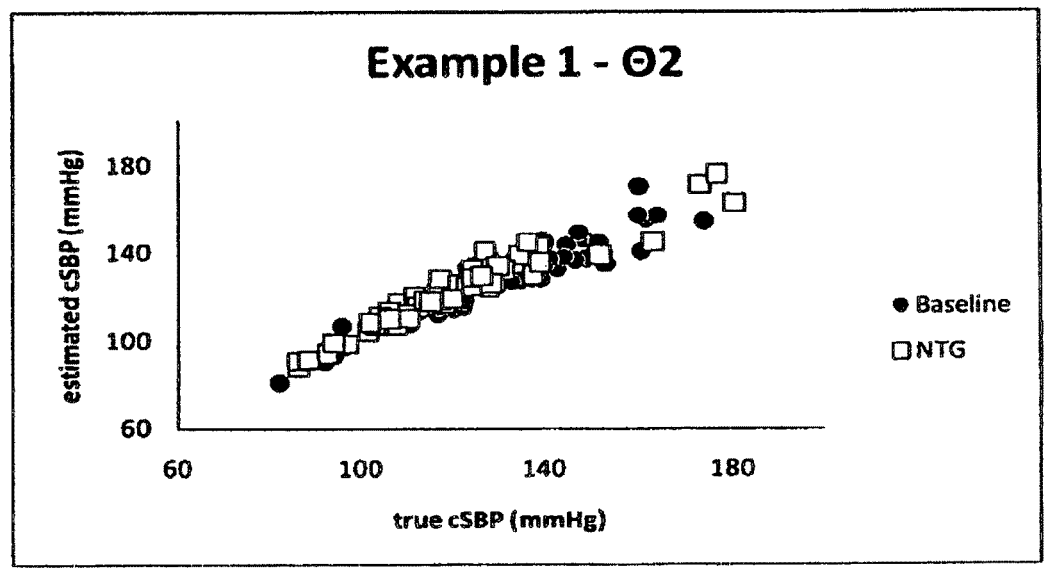

pressure waveform of the subject's pulse provides an estimate of the central systolic blood pressure of the subject.

18 Claims, 2 Drawing Sheets

(56) References Cited

U.S. PATENT DOCUMENTS

| | | | |
|---|---|---|---|
| 6,045,510 A | | 4/2000 | Ogura et al. |
| 2002/0177781 A1 | | 11/2002 | Kazuhiko |
| 2003/0023173 A1* | | 1/2003 | Bratteli .................. A61B 5/021 600/485 |
| 2003/0097074 A1* | | 5/2003 | Oka .................. A61B 5/02116 600/490 |
| 2005/0283087 A1 | | 12/2005 | Takazawa |
| 2006/0224070 A1 | | 10/2006 | Sharrock et al. |
| 2006/0264771 A1 | | 11/2006 | Lin et al. |
| 2008/0306393 A1 | | 12/2008 | Ting et al. |
| 2009/0287097 A1* | | 11/2009 | Lowe .................... A61B 5/022 600/493 |

FOREIGN PATENT DOCUMENTS

| | | |
|---|---|---|
| JP | 2004-121866 | 4/2004 |
| JP | 2005-278965 | 10/2005 |
| WO | WO2006/072776 | 7/2006 |

OTHER PUBLICATIONS

Pauca, Alfredo L. et al., Does Radial Artery Pressure Accurately Reflect Aortic Pressure? Chest, vol. 102, Issue 4, 1193-1198 (Pauca).*

Karamanoglu, M. M. A. R., et al. "An analysis of the relationship between central aortic and peripheral upper limb pressure waves in man." European heart journal 14.2 (1993): 160-167. (Year: 1993).*

Brett et al., Estimating central systolic blood pressure during oscillometric determination of blood pressure: proof of concept and validation by comparison with intra-aortic pressure recording and arterial tonometry, Blood Pressure Monitoring, 2012, pp. 132-136, vol. 17, No. 3.

English Language Translation of Japanese Office Action (Notice of Reason for Rejection) for corresponding pending Japanese Patent Application No. 2011-536943, dated Aug. 19, 2014, 3 pages.

International Search Report for related PCT Application No. PCT/GB2009/002703, dated Jan. 20, 2010.

Jin-Oh-Hahn et al., A New Approach to Reconstruction of Central Aortic Blood Pressure Using "Adaptive" Transfer Function, Engineering in Medicine and Biology Society, EMBS, 2008, 30$^{th}$ Annual International Conference of the IEEE, Piscataway, NJ, USA, Aug. 20, 2008, pp. 813-816, XP031508079.

Karamanoglu et al., On-line Synthesis of the Human Ascending Aortic Pressure Pulse From the Finger Pulse, Hypertension, 1997, pp. 1416-1424, vol. 6, No. 30.

Miyashita et al., Aging and Arterial Pressure Waveform—Augmentation Index, Modern Physician, 2004, pp. 1699-1704, vol. 24, No. 11.

Notice of Reason for Rejection issued in related Japanese Application No. 2011-536943, dated Oct. 1, 2013.

O'Rourke et al. Pulse wave analysis, Journal of Hypertension, 1996, pp. S147-S157, vol. 14, Suppl 5.

Yaginuma et al., Genesis of the Arterial Pressure Waveform and Transmission Changes to Measurement Points, Blood Pressure, 2001, pp. 1035-1040, vol. 8, No. 10.

* cited by examiner

METHODS FOR MEASURING BLOOD PRESSURE

The present invention relates to an apparatus and a method for measuring and estimating the blood pressure of a subject and more specifically relates to an apparatus and a method for estimating the central systolic blood pressure of a subject.

Blood pressure (BP) refers to the force exerted by circulating blood on the walls of blood vessels, and constitutes one of the principal vital signs. The pressure of the circulating blood decreases as blood moves through arteries, arterioles, capillaries, and veins. The term blood pressure generally refers to arterial pressure, i.e., the pressure in the larger arteries. Arteries are the blood vessels which take blood away from the heart.

Blood pressure in the arteries changes in a generally oscillatory manner and can be displayed as a waveform (a graph of pressure against time). The peak pressure in the arteries is known as the systolic blood pressure (SBP) and occurs near the beginning of the cardiac cycle. The lowest pressure in the arteries, which occurs at the resting phase of the cardiac cycle, is known as the diastolic blood pressure (DBP). The average pressure throughout the cardiac cycle is known as the mean arterial pressure (MAP), and the pulse pressure (PP) is the difference between the systolic and diastolic pressures.

Existing blood pressure monitors provide a measure of systolic and diastolic blood pressure in the peripheral arteries, e.g. the arm. However, it has long been recognised that systolic blood pressure measured at the brachial artery, radial artery or digital artery exceeds central systolic blood pressure (cSBP) at the aortic root because systolic blood pressure is amplified above that close to the heart by propagation along the peripheral arteries in the upper limb as a result of reflected pressure waves. This also results in a difference in the central pulse pressure compared to the peripheral pulse pressure. Diastolic blood pressure is similar at central and peripheral sites because of the slow rate of change of pressure during diastole. Mean arterial pressure is also similar at central and peripheral sites. cSBP would be expected to provide a better indication of the load on the heart and hence be more closely related to heart disease than peripheral systolic blood pressure (pSBP).

Until recently, the only way of measuring central blood pressure was by placing a catheter in the aorta. However, a non-invasive method (SphygmoCor®, Atcor, Australia) is now available to estimate cSBP. Data obtained using this system suggests that cSBP is indeed more important than pSBP. In the CAFÉ study, for example, an antihypertensive regime producing better outcome (i.e. fewer cardiovascular deaths and events) was associated with lower central but not arm pressure [1]. In the STRONG heart study, cSBP was a better predictor of cardiovascular death than pSBP [2]. As a result of these studies it appears that it would be advantageous to use central blood pressure as an outcome measure for cardiovascular drugs.

There are several limitations of the SphygmoCor® device. It is expensive (it costs more than $30,000 compared to less than $1,000 for a conventional BP monitor), requires trained personnel to operate it and takes substantially longer to use than a conventional BP monitor. A hand held probe is placed over the radial artery at the wrist (requiring skill and training on behalf of the operator and co-operation by the patient) to produce a blood pressure waveform. This waveform is then calibrated, usually from a conventional BP measurement taken from the brachial artery using a standard BP monitor, and a transfer function applied to the radial pressure waveform to obtain cSBP. Further disadvantages of the system are that, if calibrated from brachial artery blood pressures, it is subject to a systematic error introduced by differences in blood pressure between the brachial and the radial arteries. The transfer function transforming radial pressure to aortic pressure is complex. There are many potential variants of this transfer function and the relative accuracy of such variants has not been established.

The present invention provides an apparatus for estimating a central systolic blood pressure (cSBP) of a human subject, the apparatus comprising:
 a non-invasive blood pressure determining device to determine a peripheral blood pressure waveform of the subject's pulse and at least two peripheral blood pressure measurements within the cardiac cycle of the subject; and
 a processor to apply a transfer function to the peripheral blood pressure waveform to provide an estimate of the central blood pressure waveform of the subject's pulse,
 wherein the at least two peripheral blood pressure measurements within the cardiac cycle and the peripheral blood pressure waveform of the subject's pulse are determined at substantially the same point on a peripheral artery of the subject, and wherein the estimate of the central blood pressure waveform of the subject's pulse provides an estimate of the central systolic blood pressure of the subject.

Surprisingly, it has been discovered by the inventors that a conventional non-invasive blood pressure determining device can be used to determine the peripheral blood pressure waveform of the subject's pulse which can be used to estimate the cSBP. This is in addition to the non-invasive blood pressure determining device being able to determine peripheral blood pressure measurements within the cardiac cycle. It was not previously thought that a conventional non-invasive blood pressure determining device could be used to estimate the cSBP of a subject. This means that a single blood pressure determining device can be used to determine both peripheral blood pressure measurements and central BP (cSBP). There is no need to use more than one device at two different locations on the body of the subject as in the SphygmoCor® system.

As a result of being able to use a conventional non-invasive blood pressure determining device in the apparatus, a number of advantages are provided. These are: no special training is required in order to use the apparatus; the apparatus itself is relatively cheap to manufacture; the apparatus is relatively quick and easy to use; and it does not introduce any systematic error as a result of differences in blood pressure between the location of peripheral blood pressure determination compared to the location of peripheral blood pressure waveform determination.

Any two different peripheral blood pressure measurements within the cardiac cycle can be used to give an estimate of the cSBP. Suitable peripheral blood pressure measurements are peripheral systolic blood pressure (pSBP), peripheral diastolic blood pressure (pDBP), and peripheral mean arterial pressure (pMAP).

In one embodiment, the non-invasive blood pressure determining device is used to determine a peripheral blood pressure waveform of the subject's pulse and at least two of: the pSBP; the pDBP; and the pMAP of the subject. In another embodiment, the non-invasive blood pressure determining device is used to determine a peripheral blood pressure waveform of the subject's pulse, the pSBP of the subject and the pDBP of the subject. In an alternative embodiment, the non-invasive blood pressure determining device is used to determine a peripheral blood pressure waveform of the subject's pulse, the pSBP of the subject and the pMAP of the subject. In yet another embodiment, the non-invasive blood pressure determining device is used to determine a peripheral blood pressure waveform of the subject's pulse, the pDBP of the subject and the pMAP of the subject. In a further embodiment, the non-invasive blood pressure determining device is used to determine the peripheral blood pressure waveform of the subject's pulse, and the pSBP, the pDBP and the pMAP of the subject. In this embodiment, all four measurements (the peripheral blood pressure waveform, the pSBP, the pDBP and the pMAP) should be determined at substantially the same point on the peripheral artery of the subject. Where three (or more) peripheral blood pressure measurements within the cardiac cycle are determined (e.g. the pSBP, the pDBP and the pMAP), a more accurate estimation of cSBP may be obtained.

The term central systolic blood pressure (cSBP) means the maximum blood pressure that occurs close to the heart in the aorta or at the aortic root and results from the systole of the heart.

The term peripheral systolic blood pressure (pSBP) means the maximum blood pressure that occurs in the peripheral arteries of the subject after the systole of the heart.

The term peripheral diastolic blood pressure (pDBP) means the minimum blood pressure that occurs in the peripheral arteries of the subject after the diastole.

The term peripheral mean arterial pressure (pMAP) means the average arterial blood pressure in the peripheral arteries of the subject over a complete cardiac pulsation.

The term peripheral arteries means the arteries which are at a distance from the heart of the subject. For example, in a human the peripheral arteries are those more than about 10 cm from the heart. The term peripheral arteries is widely used and its meaning is well known to those skilled in the art.

The term blood pressure waveform means the oscillatory wave-like curve that is obtained by plotting the pressure or a pressure related change in an artery against time. This can be in the peripheral arteries (peripheral blood pressure waveform) or in the aorta close to the heart or at the aortic root (central blood pressure waveform). The terms blood pressure waveform, peripheral blood pressure waveform and central blood pressure waveform are widely used and their meanings are well known to those skilled in the art.

The term pulse means the pressure waveforms in the arteries of the subject which result from the contraction of the heart.

The non-invasive blood pressure determining device can be any suitable non-invasive blood pressure determining device which is capable of being used to measure or determine the peripheral blood pressure waveform of the subject's pulse and at least two peripheral blood pressure measurements within the cardiac cycle of the subject (for example, at least two of: the pSBP; the pDBP; and the pMAP of the subject). Preferably, the non-invasive blood pressure determining device should be capable of being, used to measure or determine the peripheral blood pressure waveform of the subject's pulse, the pSBP, the pDBP, and the pMAP of the subject. Preferably, the non-invasive blood pressure determining device is an oscillometric non-invasive blood pressure determining device, i.e. it uses an oscillometric method. Suitable oscillometric blood pressure determining devices are well known to those skilled in the art. These are commonly referred to as oscillometric blood pressure monitors. Well known and commonly used blood pressure monitors comprise a blood pressure cuff fitted with an electronic pressure sensor (transducer). Such blood pressure monitors can be used to measure the pSBP, the pDBP and the pMAP. This is done by placing the cuff around a peripheral artery of the subject and inflating it to certain pressures which allow determination of the pSBP, the pDBP and the pMAP.

The inventors have found that blood pressure monitors, and in particular oscillometric blood pressure monitors, can be used to determine the peripheral blood pressure waveform of the subject. In reality, the pressure waveform in the cuff of a blood pressure monitor may not correspond exactly to the peripheral blood pressure waveform of the subject. However, this cuff pressure waveform will be related to the peripheral blood pressure waveform. When a transfer function is applied to this cuff pressure waveform, which is indicative of the peripheral blood pressure waveform, the transfer function can account for and remove this discrepancy between the cuff pressure waveform and the peripheral blood pressure waveform.

In one embodiment, the blood pressure determining device comprises a cuff which can be used to measure the peripheral blood pressure waveform. The peripheral blood pressure waveform can be measured by adjusting the pressure in the cuff so that it is in between the pSBP and the pDBP. At this pressure, movement of the arterial wall causes a change in volume within the cuff and hence a pressure change (a cuff pressure waveform) which is indicative of the peripheral blood pressure waveform. As discussed above, this cuff pressure waveform may not correspond exactly to the peripheral blood pressure waveform but it is closely related. A pressure sensor attached to the cuff can detect the variation of pressure and produce a waveform of the pulse in the artery. The waveform can be recorded by the processor. Preferably, the pressure in the cuff that is used to determine the peripheral blood pressure waveform is equal to the pDBP of the subject plus between 5% and 95% of the pulse pressure of the subject. For example, if the pDBP is 80 mmHg and the pSBP is 120 mmHg in a particular subject, the cuff pressure used to determine the peripheral blood pressure waveform is between 82 mmHg (80+0.05(120−80)) and 118 mmHg (80+0.95(120−80)). More preferably, the pressure in the cuff used to determine the peripheral blood pressure waveform is equal to the pDBP plus between 10% and 50% of the pulse pressure, even more preferably, the pDBP plus between 20% and 40% of the pulse pressure, and most preferably, the pDBP plus about 33% of the pulse pressure. Alternatively, the pressure in the cuff that is used to determine the peripheral blood pressure waveform of the subject is between 50 mmHg and the subject's pSBP. Preferably, the pressure in the cuff that is used to determine the peripheral blood pressure waveform of the subject is equal to or more than 50 mmHg and less than the subject's pSBP. In one embodiment, the pressure in the cuff that is used to determine the peripheral blood pressure waveform of the subject is between 50 mmHg and 65 mmHg.

The non-invasive blood pressure determining device can measure one peripheral blood pressure waveform which is then manipulated with a transfer function to estimate the central blood pressure waveform. Preferably, the non-invasive blood pressure determining device measures a plurality of peripheral blood pressure waveforms and averages them to obtain a single average peripheral blood pressure waveform. The processor then applies the transfer function to the average peripheral blood pressure waveform. Preferably, the non-invasive blood pressure determining device determines at least 2 waveforms, more preferably, at least 5 waveforms, and most preferably, at least 10 waveforms. Preferably, the non-invasive blood pressure determining device determines between 2 and 30 waveforms, more preferably, between 2 and 20 waveforms, more preferably still, between 5 and 15 waveforms, and most preferably, about 10 waveforms.

Alternatively, rather than measuring a specific number of waveforms, the non-invasive blood pressure determining device can determine the peripheral blood pressure waveform for a predetermined period of time. Preferably, the non-invasive blood pressure determining device determines the peripheral blood pressure waveform for between 2 and 30 seconds, more preferably, the peripheral blood pressure waveform is determined for between 5 and 20 seconds, more preferably still, the peripheral blood pressure waveform is determined for between 5 and 15 seconds, even more preferably, the peripheral blood pressure waveform is determined for between 10 and 15 seconds and, most preferably, the peripheral blood pressure waveform is determined for about 10 seconds. Alternatively, the non-invasive blood pressure determining device may determine the peripheral blood pressure waveform for at least 2 seconds, more preferably, at least 5 seconds, and most preferably, at least 10 seconds. The number of waveforms measured in the particular predetermined period of time can then averaged.

The advantage provided by measuring a plurality of waveforms and averaging them is that better results are achieved as any differences due to short term beat-to-beat variations in pressure are reduced.

The exact size and nature of blood pressure determining device will depend on the location on the subject that the at least two peripheral blood pressure measurements within the cardiac cycle of the subject (e.g. at least two of: the pSBP, the pDBP and the pMAP) and the peripheral blood pressure waveform are measured. For example, the blood pressure determining device may be adapted to measure the relevant blood pressure parameters at the upper arm of a human. The blood pressure determining device is adapted to determine the relevant blood pressure parameters at a peripheral artery of the human. Preferably, the peripheral artery is selected from the brachial artery, the radial artery, the digital artery, the femoral artery, the popliteal artery, the dorsalis pedis artery and the posterior tibial artery. More preferably, the peripheral artery is the brachial artery (located in the upper arm).

Surprisingly, the inventors have found that the peripheral blood pressure waveform can be determined at numerous peripheral arteries on a subject. Previously, most peripheral arteries were not considered to give a pulse which was sufficiently clear, well defined and strong enough to allow determination of the peripheral waveform.

The advantage provided by being able to use a standard blood pressure determining device is that it allows central blood pressure to be determined at the same time, or with very little delay, and with the same ease as a conventional blood pressure measurement.

Furthermore, as the only additional requirement to a standard blood pressure monitor is a processor, or use of the existing processor to perform the necessary calculations, there is little additional manufacturing cost.

The processor can be any suitable processor so that it can: receive information from the blood pressure determining device regarding the peripheral blood pressure waveform and the at least two peripheral blood pressure measurements within the cardiac cycle (e.g. at least two of: the pSBP, the pDBP and the pMAP); and make the necessary calculations to apply a transfer function to the peripheral blood pressure waveform, thereby producing an estimate of the central blood pressure waveform of the subject's pulse.

More specifically, when the blood pressure determining device measures the peripheral blood pressure waveform of the artery, this waveform is relative. It does not provide absolute values of pressure. The at least two different peripheral blood pressure measurements within the cardiac cycle (e.g. at least two of: the pSBP, the pDBP and the pMAP) are used as reference points on the waveform so that the waveform can be used as an absolute measure of the blood pressure waveform in the artery. The processor can then apply the transfer function to the absolute peripheral waveform to give an estimate of the absolute central blood pressure waveform. From this waveform, the peak pressure corresponds to the estimate of the cSBP. Suitable processors are well known to those skilled in the art. For example, the processor may be a microprocessor, or discrete analogue or digital circuitry. Preferably, the processor is a microprocessor. Some standard blood pressure determining devices already contain processors. Therefore, with suitable adjustment (e.g. by using suitable software), such a processor can be used in the method described above.

If the apparatus measures a plurality of peripheral blood pressure waveforms, the processor will record the plurality of waveforms and average them to obtain a single average peripheral blood pressure waveform to which the transfer function can be applied. Alternatively, the processor can apply the transfer function to each waveform in a plurality of peripheral blood pressure waveforms to obtain a plurality of estimates of the central blood pressure waveform which can then be averaged to obtain an average central blood pressure waveform.

Preferably, the processor controls the operation of the non-invasive blood pressure determining device to allow it to determine the at least two peripheral blood pressure measurements within the cardiac cycle (e.g. at least two of: the pSBP, the pDBP and the pMAP) and the peripheral blood pressure waveform of the subject's pulse. For example, in one embodiment in which the non-invasive blood pressure determining device comprises a cuff, the processor controls the inflation and deflation of the cuff to determine the at least two peripheral blood pressure measurements (e.g. at least two of: the pSBP, the pDBP and the pMAP). The processor also controls the inflation of the cuff to a pressure between the pSBP and the pDBP to determine the peripheral blood pressure waveform. Alternatively, the processor controls the inflation of the cuff to a pressure between 50 mmHg and the pSBP to determine the peripheral blood pressure waveform. In one embodiment, the processor controls the inflation of the cuff to a pressure between 50 mmHg and 65 mmHg.

The processor can be connected to the non-invasive blood pressure determining device in any suitable way so that the apparatus can function. The processor can be connected directly or indirectly. For example, the processor can be connected directly to the blood pressure determining device via wires. Alternatively, the processor can be connected indirectly to the blood pressure determining device using a wireless interaction. In this way, the processor is connected to the non-invasive blood pressure determining device in a functional sense in that the apparatus functions properly but the processor is not physically connected to the non-invasive blood pressure determining device.

The transfer function can be any suitable transfer function for giving an estimate of the central blood pressure waveform from the peripheral blood pressure waveform. The exact nature of the transfer function will vary depending on the position on the subject at which the relevant blood pressure parameters are measured. The transfer function removes the amplification associated with transmission of the subject's pulse from the heart to a peripheral artery. When the pulse is considered in the frequency domain (i.e. as the sum of a series of harmonic waveforms of frequency equal to a multiple of the frequency of the pulse), it is apparent that only the rapidly changing components of the pulse are amplified. By using a transfer function which attenuates high frequency components of the pulse the amplification can be removed and the central pulse recovered. The simplest form of transfer function is a low-pass filter such as a Butterworth filter. Preferably, the filter is a low-pass Butterworth $1^{st}$ order filter and more preferably, a low-pass Butterworth $1^{st}$ order filter with cut-off frequency of 3.12 Hz and gain of 0 dB. Other types of low pass filter such as Bessel ($1^{st}$ order 3.12 Hz cut off frequency), Chebyshev ($1^{st}$ order, 3 dB ripple, 3.12 cut off frequency), Elliptic ($1^{st}$ order, 3 dB ripple in the passband, 40 db ripple in the stopband, 3.12 cut off frequency) and 0.14*(sample frequency) points moving average may also be used. Alternatively, different cut off frequencies can be used. More complex filters or algorithms may instead be used such as a transfer function derived in the time domain or in the frequency domain (by Fourier analysis).

In one embodiment, the apparatus can also give an estimate of the peripheral augmentation index (pAI) measured in percent. The AI can be estimated using any suitable method. For example, the AI is usually estimated from the late systolic shoulder of a peripheral blood pressure waveform. However, a disadvantage of this method is that the late systolic shoulder can be difficult to identify [3]. An alternative and preferred method for estimating AI, which does not require identification of the late systolic shoulder, is to use the relationship:

$$pAI=(cSBP-DBP)/(pSBP-DBP)\times 100$$

where DBP is the diastolic blood pressure and is substantially the same at peripheral and central sites [3].

The present invention also provides a method of estimating a central systolic blood pressure (cSBP) of a subject, the method comprising the steps of:
 determining a peripheral blood pressure waveform of the subject's pulse and at least two peripheral blood pressure measurements within the cardiac cycle of the subject; and
 manipulating the peripheral blood pressure waveform with a transfer function to provide an estimate of the central blood pressure waveform of the subject's pulse, wherein the at least two peripheral blood pressure measurements within the cardiac cycle of the subject and the peripheral blood pressure waveform of the subject's pulse are determined at substantially the same point on a peripheral artery of the subject, and wherein the estimate of the central blood pressure waveform of the subject's pulse provides an estimate of the central systolic blood pressure of the subject.

As discussed above, the advantage provided by determining the at least two peripheral blood pressure measurements and the peripheral blood pressure waveform at substantially the same point on a peripheral artery is that it makes the method simpler to use as a single piece of equipment can be used and a systematic error is not introduced by differences in blood pressure between the location of peripheral blood pressure measurement determination compared to the location of peripheral blood pressure waveform determination.

The at least two peripheral blood pressure measurements (e.g. at least two of: the pSBP, the pDBP and the pMAP) and the peripheral blood pressure waveform of the subject's pulse can be determined in any suitable way. Preferably, a non-invasive blood pressure determining device is used, and more preferably, an oscillometric non-invasive blood pressure determining device is used. The ways in which these devices can be used are described above. Preferably, the at least two peripheral blood pressure measurements (e.g. at least two of: the pSBP, the pDBP and the pMAP) and the peripheral blood pressure waveform of the subject's pulse are determined using a single blood pressure determining device. The use of a single blood pressure determining device allows the three or more blood pressure parameters to be determined at the same point on a peripheral artery of the subject.

If a non-invasive blood pressure determining device is used to determine the peripheral blood pressure waveform and which comprises a cuff, the step of determining the peripheral blood pressure waveform preferably comprises adjusting the pressure in the cuff so that it is in between the pSBP and the pDBP. The preferred values of the pressure in the cuff are described above.

Preferably, the step of determining a peripheral blood pressure waveform of the subject's pulse comprises: recording a plurality of peripheral blood pressure waveforms; and averaging the waveforms to obtain a single average peripheral blood pressure waveform, wherein the average peripheral blood pressure waveform is manipulated with the transfer function. Alternatively, the step of determining a peripheral blood pressure waveform of the subject's pulse comprises: recording the peripheral blood pressure waveform for a predetermined period of time; and averaging the waveforms determined in the predetermined period of time to obtain a single average peripheral blood pressure waveform, wherein the average peripheral blood pressure waveform is manipulated with the transfer function. The preferred features of these steps are discussed above.

The peripheral blood pressure waveform can be manipulated with a transfer function in any suitable way to provide an estimate of the central blood pressure waveform of the subject's pulse. Preferably, the peripheral blood pressure waveform is manipulated using a processor. The transfer function is discussed above.

The peripheral artery of the subject, at which the at least two peripheral blood pressure measurements (e.g. at least two of: the pSBP, the pDBP and the pMAP) and the peripheral blood pressure waveform are determined, can be any suitable artery. The peripheral artery is preferably selected from the brachial artery, the radial artery, the digital artery, the dorsalis pedis artery, the posterior tibial artery, the popliteal artery and the femoral artery. More preferably, the peripheral artery is the brachial artery.

Preferably, the method further comprises the step of calculating the peripheral augmentation index (pAI) using the relationship: pAI=(cSBP−DBP)/(pSBP−DBP)×100.

The present invention also provides a device for use with a non-invasive blood pressure determining device for estimating a central systolic blood pressure of a subject, the device comprising:
 a processor to apply a transfer function to a peripheral blood pressure waveform of the subject's pulse to provide an estimate of a central waveform of the subject's pulse which provides an estimate of the central systolic blood pressure of the subject,
 wherein the processor is for attachment to a non-invasive blood pressure determining device which determines at least two peripheral blood pressure measurements within the cardiac cycle of a subject and the peripheral blood pressure waveform of a subject's pulse at substantially the same point on a peripheral artery.

Preferably, the at least two peripheral blood pressure measurements are at least two of: the pSBP, the pDBP and the pMAP. In one embodiment, three peripheral blood pressure measurements within the cardiac cycle of a subject can be determined, for example, the pSBP, the pDBP and the pMAP.

Further, the present invention provides the use of a non-invasive blood pressure determining device in the above described method.

Additionally, the present invention provides a non-invasive blood pressure determining device for use in the estimation of a central systolic blood pressure of a subject, wherein the blood pressure determining device can determine at least two peripheral blood pressure measurements within the cardiac cycle of a subject and a peripheral blood pressure waveform of a subject's pulse.

Preferably, the at least two peripheral blood pressure measurements are at least two of: the pSBP, the pDBP and the pMAP. In one embodiment, three peripheral blood pressure measurements within the cardiac cycle of a subject can be determined, for example, the pSBP, the pDBP and the pMAP.

Figure 2:
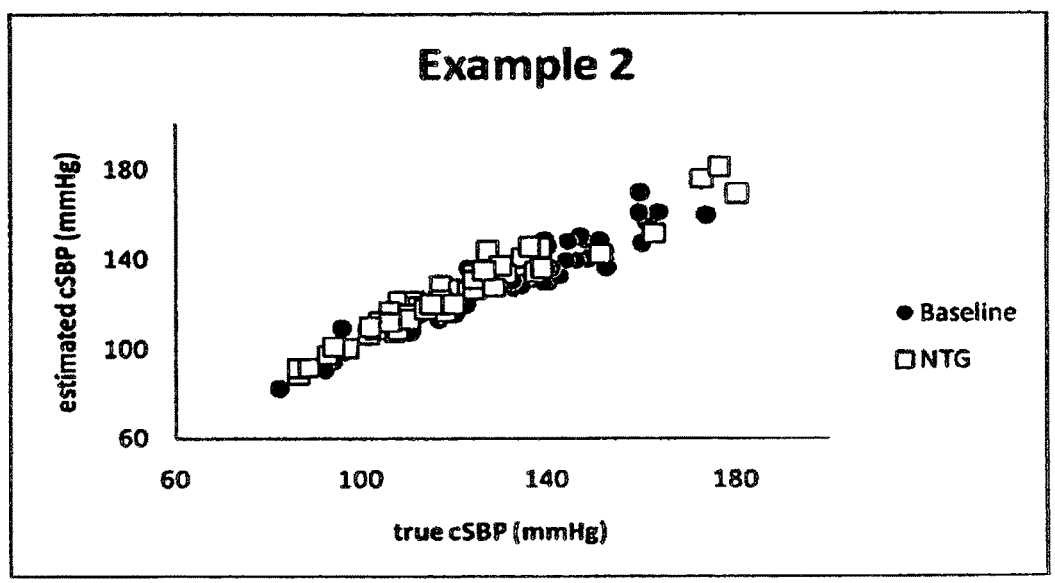

The present invention will now be described, by way of example only, with reference to the figures in which:

FIG. 1 is a graph showing agreement between estimates of cSBP obtained from an arm cuff using the method described in Example 1 and measured values of cSBP obtained by placing a pressure transducer directly in the aorta of 29 subjects at the time of cardiac catheterisation. Measurements are obtained at rest and after administration of nitroglycerin (NTG, a vasodilating drug that lowers cSBP); and FIG. 2 is a graph showing agreement between estimates of cSBP obtained from an arm cuff using the method described in Example 2 and measured values of cSBP obtained by placing a pressure transducer directly in the aorta of 29 subjects at the time of cardiac catheterisation.

EXAMPLE 1

The inventors have developed a simple signal processing algorithm which allows cSBP to be determined using exactly the same technology as is incorporated within a standard oscillometric BP monitor. This potentially allows cSBP to be determined at the same time and with the same ease as a conventional BP measurement. Furthermore, as the only additional requirement is signal processing, there is no additional manufacturing cost, only the initial software development and packaging. The algorithm has been compared with direct measurements of cSBP obtained with a high fidelity pressure tipped catheter placed in the aortic root. The method overcomes the problems associated with the SphygmoCor system in that it is inexpensive, requires no user training and produces small systematic error.

The method is based on making a standard oscillometric determination of blood pressure in the arm of a human patient to determine peripheral systolic (pSBP) and diastolic (pDBP) blood pressure. This is done using a cuff and the method is well known. The cuff is then inflated to a fixed pressure usually equal to (pDBP+⅓×(pSBP−pDBP), 65 mmHg, pMAP or pDBP and the pressure inside the cuff recorded for a minimum of 10 cardiac cycles. The waveforms thus acquired are ensemble averaged to obtain a single average peripheral cuff waveform (apcp). A generalised transfer function (GTF) is then applied to the peripheral waveform to obtain an estimate of a central waveform. Central systolic BP (cSBP) is determined from the maximum of this waveform.

The GTF was determined by comparing peripheral waveforms obtained from the arm cuff with central waveforms (cp) measured directly by placing a pressure transducer in the aortic arch at the time of cardiac catheterisation in a sample of subjects representative of the general population in which estimation of cBP was required. Details of the computational procured are given below:

Methods for Obtaining a Generalised Transfer Function

Peripheral cuff pressure waveforms, which are closely related to peripheral blood pressure waveforms, are acquired during a period of about 10 seconds so that a plurality of waveforms are acquired. Each pressure pulse is then identified in order to average them to obtain an average pressure pulse for the algorithm to work on. From there, there are 2 methods:

Method One

For this method, calculations are mainly made in the frequency domain using a transfer function H so that:

$$CP = H \times PP$$

Where CP and PP are respectively a normalised central pressure pulse and a normalised peripheral pressure pulse in the frequency domain.

The transfer function H is obtained by making calculations on a given set of measurements (here measurements from p-patients) as follows:

Be FFT( ) the fast Fourier transform function and $FFT^{-1}$( ) the inverse fast Fourier transform function, Be $H_{i=1\ldots p}$ p-complex vectors of length n, each $H_i$ represents the individual transfer function for every ($cP_i, pP_i$) such as:

$$CP_i = H_i \times PP_i$$

Where: $CP_i = FFT(cP_i)$ and $PP_i = FFT(pP_i)$ $H_i$ are thus defined as: $H_i = CP_i / PP_i$ H is then the average transfer function (i.e. moduli and phases are averaged) of all the individual transfer functions.

N.B.: All the preceding calculations are made on vectors but elements-by-elements not according to the usual matrix-vector algebra.

To determine an estimate of the central blood pressure pulse (ecP(t)) from a peripheral pulse (pP(t)) the algorithm proceeds as follow:

$$PP = FFT(pP)$$

$$ECP = H \times PP$$

$$ecP(t) = FFT^{-1}(ECP)$$

ecP(t) is then calibrated from mean arterial and diastolic blood pressures.

Method Two

For this method all the calculations remain in the time domain as to obtain an estimate of the central blood pressure pulse one applies an IIR filter (ARX model) to the peripheral pulse.

Coefficients ($a_i$ and $b_i$) of this IIR filter are obtained by making calculations on a given set of measurements (here measurements from p patients) as follow:

Be X the coefficients matrix such as:

$$X = \begin{bmatrix} a_1 \\ a_2 \\ \ldots \\ a_n \\ b_1 \\ b_2 \\ \ldots \\ b_m \end{bmatrix}$$

Be Y the normalised central pressure pulse (cP(t)) matrix containing central pulses of p-patients such as:

$$Y = \begin{bmatrix} cP(t_1)_{p1} \\ cP(t_2)_{p1} \\ \ldots \\ cP(t_{T1})_{p1} \\ \ldots \\ cP(t_1)_{pp} \\ cP(t_2)_{pp} \\ \ldots \\ cP(t_{Tp})_{pp} \end{bmatrix}$$

Be A a matrix describing the IIR filter structure such as:

$$A = \begin{bmatrix} cP(t_1-1)_{p1} & \cdots & cP(t_1-n)_{p1} & pP(t_1)_{p1} & pP(t_1-1)_{p1} & \cdots & pP(t_1-m+1)_{p1} \\ cP(t_2-1)_{p1} & \cdots & cP(t_2-n)_{p1} & pP(t_2)_{p1} & pP(t_2-1)_{p1} & \cdots & pP(t_2-m+1)_{p1} \\ \ldots & \ldots & \ldots & \ldots & \ldots & \ldots & \ldots \\ cP(t_{T1}-1)_{p1} & \cdots & cP(t_{T1}-n)_{p1} & pP(t_{T1})_{p1} & pP(t_{T1}-1)_{p1} & \cdots & pP(t_{T1}-m+1)_{p1} \\ \ldots & \ldots & \ldots & \ldots & \ldots & \ldots & \ldots \\ cP(t_1-1)_{pp} & \cdots & cP(t_1-n)_{pp} & pP(t_1)_{pp} & pP(t_1-1)_{pp} & \cdots & pP(t_1-m+1)_{pp} \\ cP(t_2-1)_{pp} & \cdots & cP(t_2-n)_{pp} & pP(t_2)_{pp} & pP(t_2-1)_{pp} & \cdots & pP(t_2-m+1)_{pp} \\ \ldots & \ldots & \ldots & \ldots & \ldots & \ldots & \ldots \\ cP(t_{Tp}-1)_{pp} & \cdots & cP(t_{Tp}-n)_{pp} & pP(t_{Tp})_{pp} & pP(t_{Tp}-1)_{pp} & \cdots & pP(t_{Tp}-m+1)_{pp} \end{bmatrix}$$

Where pP(t) is the normalized peripheral pressure pulse. Coefficients are thus obtained by solving:

$$Y = A \cdot X$$

So:

$$X = (A^t \cdot A)^{-1} \cdot A^t \cdot Y$$

The IIR filter is then applied to cP(t) and returns ecP(t) which is then calibrated from arterial mean and diastolic blood pressure.

The number of coefficients (n and m) is chosen so that the RMS error of the estimated central pulse (filtered one) compared with the actual central pulse is minimum on the whole set of p-measurements.

The accuracy of this method for measuring cBP non-invasively was assessed by comparing non-invasive with invasive measurements obtained at the time of cardiac catheterisation using a high fidelity catheter placed in the aortic root. This was done in 29 subjects both at rest and after administration of nitroglycerin (500 mcg sublingually), a vasodilating drug that lowers cBP. To remove errors associated with determination of peripheral blood pressure in the arm, the cuff waveforms were normalized prior to applying the GTF and the pressure waveform obtained after applying the transfer function was then calibrated from mean and diastolic blood pressure. The mean difference between non-invasive and invasive measures of cSBP was −2.9 mmHg in method 1 and −3.6 mmHg in method 2 with standard deviation (SD) of this difference 6.5 mmHg in method 1 and 7.0 mmHg in method 2 for measurements made at baseline. During nitroglycerin, the mean difference and SD were 2.7 and 4.8 mmHg respectively in method 1 and 2.2 and 5.8 mmHg respectively in method 2.

EXAMPLE 2

In this method, peripheral waveforms are acquired in the same way as in Example 1. A standard oscillometric determination of blood pressure in the arm is conducted to determine peripheral systolic (pSBP) and diastolic blood pressure (DBP—which is the same at central and peripheral sites). This is done using a cuff and the method is well known. The cuff is then inflated to a fixed pressure usually equal to 65 mmHg, the DBP or the pMAP and the pressure inside the cuff recorded for approximately 10 seconds. The waveforms thus acquired are ensemble averaged to obtain a single average peripheral cuff waveform. This waveform is filtered using a low pass Butterworth $1^{st}$ order filter with cut-off frequency 3.12 Hz and gain of 0 dB and pSBP is taken as the peak of the filtered waveform. This filtering of the waveform effectively removes amplification associated with transmission from the heart to the brachial artery. Whilst a Butterworth low-pass filter is one method for filtering the waveform other filters with similar characteristics are expected to produce similar results.

The accuracy of this method for measuring cBP non-invasively was assessed by comparing non-invasive with invasive measurements obtained at the time of cardiac catheterisation using a high fidelity catheter placed in the aortic root. This was done in 29 subjects both at rest and after administration of nitroglycerin (500 mcg sublingually), a vasodilating drug that lowers cBP. To remove errors associated with determination of peripheral blood pressure in the arm, the cuff waveforms were normalized prior applying the GTF and the pressure waveform obtained after applying the transfer function was then calibrated from mean and diastolic blood pressure. The mean difference between non-invasive and invasive measures of cSBP was −1.5 mmHg with standard deviation (SD) of this difference 6.8 mmHg for measurements made at baseline. During nitroglycerin, the mean difference and SD were 4.4 and 5.1 mmHg respectively.

The graph of FIG. 2 shows agreement between estimates of cSBP obtained from an arm cuff using the above approach and measured values of cSBP obtained by placing a pressure tranducer directly in the aorta.

Once cSBP is known, the method can be used to measure augmentation index (AI) (since AI is now known to be related to cSBP, pSBP and DBP) by the relationship: AI=(cSBP−DBP)/(pSBP−DBP). AI is an additional measurement provided by the SphygmoCor system. In the SphygmoCor, AI is obtained from the late systolic shoulder of the radial pressure waveform but is sometimes difficult to identify, The above method thus provides a more robust measure of AI which can always be determined once the central and peripheral blood pressures are determined.

REFERENCES

1. Williams B, Lacy P S, Thom S M, Cruickshank K, Stanton A, Collier D, Hughes A D, Thurston H, O'Rourke M. Differential impact of blood pressure-lowering drugs on central aortic pressure and clinical outcomes: principal results of the Conduit Artery Function Evaluation (CAFE) study. Circulation. 2006; 113:1213-1225.
2. Roman M J, Devereux R B, Kizer J R, Lee E T, Galloway J M, Ali T, Umans J G, Howard B V. Central pressure more strongly relates to vascular disease and outcome than does brachial pressure: the Strong Heart Study. Hypertension. 2007; 50:197-203.
3. Munir S, Guilcher A, Kamalesh T et al. Peripheral augmentation index defines the relationship between central and peripheral pulse pressure. Hypertension 2008 January; 51(1):112-8.

The invention claimed is:

1. A method of estimating a central systolic blood pressure (cSBP) of a human subject comprising:
   obtaining a peripheral blood pressure waveform of a pulse of a human subject and at least two peripheral blood pressure measurements over at least one cardiac cycle of the human subject from a blood pressure cuff placed about an arm of the human subject about a brachial artery when pressure in the blood pressure cuff is inflated to a sub-systolic pressure;
   applying a transfer function to the obtained peripheral blood pressure waveform to provide an estimate of a central blood pressure waveform of the subject;
   calibrating the obtained peripheral blood pressure waveform using the at least two peripheral blood pressure measurements, wherein the at least two peripheral blood pressure measurements comprise at least two of peripheral systolic blood pressure (pSBP), peripheral diastolic blood pressure (pDBP) and peripheral mean arterial pressure (pMAP); and
   electronically estimating the cSBP of the human subject using the calibrated peripheral blood pressure waveform and the estimate of the central blood pressure waveform.

2. The method of claim 1, wherein the obtaining, applying, calibrating and estimating are carried out using at least one processor in communication with the blood pressure cuff.

3. The method of claim 1, which the obtaining is carried out when inflation pressure in the blood pressure cuff is adjusted to a pDBP of the human subject plus between 5% and 95% of a pulse pressure of the human subject.

4. The method of claim 1, wherein the at least two peripheral blood pressure measurements are only pSBP and pDBP.

5. The method of claim 1, wherein the at least two peripheral blood pressure measurements are only pDBP and pMAP.

6. The method of claim 1, wherein the obtaining the peripheral blood pressure waveform of the subject's pulse comprises recording a least 10 peripheral blood pressure waveforms corresponding to at least 10 cardiac cycles and averaging the waveforms to obtain a single average peripheral blood pressure waveform, and wherein the calibration and the applying actions are carried out using the average peripheral blood pressure waveform.

7. The method of claim 1, further comprising electronically calculating a peripheral augmentation index (AI) using the relationship; AI=(cSBP−DBP)/(pSBP−DBP).

8. The method of claim 1, wherein the transfer function has a cutoff frequency of 3.12 Hz and a gain of 0 db.

9. The method of claim 1, wherein the transfer function comprises a Butterworth $1^{st}$ order filter.

10. A method of estimating a central systolic blood pressure (cSBP) comprising:
    obtaining a peripheral blood pressure waveform of a pulse of a human subject and at least two peripheral blood pressure measurements over at least one cardiac cycle of the human subject from a blood pressure cuff placed about a brachial artery of an arm of the human subject when pressure in the blood pressure cuff is inflated to a sub-systolic pressure;
    calibrating the obtained peripheral blood pressure waveform using the at least two peripheral blood pressure measurements, wherein the at least two peripheral blood pressure measurements comprise at least two of peripheral systolic blood pressure (pSBP), peripheral diastolic blood pressure (pDBP) and peripheral mean arterial pressure (pMAP);
    applying a transfer function to the obtained peripheral blood pressure waveform to provide an estimate of a central blood pressure waveform; and
    electronically estimating the cSBP of the human subject using the peripheral blood pressure waveform and with the calibration and the estimate of the central blood pressure waveform.

11. The method of claim 10, wherein the obtaining, applying, calibrating and estimating are carried out using at least one processor in communication with the blood pressure cuff.

12. The method of claim 10, which the obtaining is carried out when pressure in the blood pressure cuff is adjusted to a pDBP of the human subject plus between 5% and 95% of a pulse pressure of the human subject.

13. The method of claim 10, wherein the at least two peripheral blood pressure measurements are only pSBP and pDBP or only pDBP and pMAP.

14. The method of claim 11, wherein the obtaining the peripheral blood pressure waveform of the subject's pulse comprises recording a least 10 peripheral blood pressure waveforms corresponding to at least 10 cardiac cycles and averaging the waveforms to obtain a single average peripheral blood pressure waveform, and wherein the calibration and the applying actions are carried out using the average peripheral blood pressure waveform.

15. The method of claim 10, further comprising electronically calculating a peripheral augmentation index (AI) using the relationship; AI=(cSBP−DBP)/(pSBP−DBP).

16. The method of claim 10, wherein the transfer function has a cutoff frequency of 3.12 Hz and a gain of 0 db and/or wherein the transfer function comprises a Butterworth $1^{st}$ order filter.

17. The method of claim 1, further comprising electronically displaying the estimated cSBP of the human subject.

18. The method of claim 1, further comprising electronically providing the estimated cSBP of the human subject via an oscillometric BP monitor.

* * * * *

UNITED STATES PATENT AND TRADEMARK OFFICE
CERTIFICATE OF CORRECTION

PATENT NO. : 10,213,116 B2
APPLICATION NO. : 15/019541
DATED : February 26, 2019
INVENTOR(S) : Chowienczyk et al.

Page 1 of 1

It is certified that error appears in the above-identified patent and that said Letters Patent is hereby corrected as shown below:

In the Claims

Column 14, Line 39, Claim 10:
Please correct "waveform and with" to read -- waveform with --

Column 14, Line 55, Claim 14:
Please correct "a least" to read -- at least --

Column 14, Lines 62-63, Claim 15:
Please correct "using the relationship;" to read -- using; --

Column 14, Line 66, Claim 16:
Please correct "1$^{St}$" to read -- 1$^{st}$ --

Signed and Sealed this
Eighteenth Day of June, 2019

Andrei Iancu
*Director of the United States Patent and Trademark Office*